US007813783B2

(12) United States Patent
Thomas et al.

(10) Patent No.: US 7,813,783 B2
(45) Date of Patent: Oct. 12, 2010

(54) METHODS AND SYSTEMS FOR ATTENUATION CORRECTION IN MEDICAL IMAGING

(75) Inventors: Alicia Maria Thomas, Wauwatosa, WI (US); Patrick Joseph O'Day, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 815 days.

(21) Appl. No.: 11/591,732

(22) Filed: Nov. 2, 2006

(65) Prior Publication Data

US 2008/0107229 A1     May 8, 2008

(51) Int. Cl.
*A61B 5/05* (2006.01)
*A61B 6/00* (2006.01)
(52) U.S. Cl. .......................................... 600/407; 378/4
(58) Field of Classification Search .................. 600/407
See application file for complete search history.

(56) References Cited

U.S. PATENT DOCUMENTS

2004/0258286 A1   12/2004   Salla et al.

OTHER PUBLICATIONS

Wilson, John W., Terrence Z. Wong, Salvador Borges-Neto, Timothy G. Turkington. "An Algorithm for Correction of PET/CT Mismatch Induced Cardiac Attenuation Correction Artifacts." Image Generation: General PET/CT Image Reconstruction Methods. Society of Nuclear Medicine Annual Meeting. Toronto, ON. Jun. 19, 2005.
Moller, Axel Mrtinez, Maria-Jose Martinez, Sibylle I Ziegler, Nassir Navab, Markus Schwaiger, Stephan G. Nekolla. "Emission Driven Motion Correction in PET/CT Cardiac Imaging." Image Generation: Effects of Motions and Motion Correction in PET and SPECT. Society of Nuclear Medicine Annual Meeting. Toronto, ON Jun. 19, 2005.

*Primary Examiner*—Long V Le
*Assistant Examiner*—Hien Nguyen
(74) *Attorney, Agent, or Firm*—Dean D. Small; Small Patent Law Group

(57) ABSTRACT

Methods and systems for imaging a patient are provided. The method includes scanning a patient and acquiring a plurality of frames of cine computed tomography (CT) images during one complete respiratory cycle. In one embodiment, a method is provided that includes selecting an organ of interest in the cine CT data and selecting a value for each pixel in the organ of interest that represents the maximum density measurement. An attenuation corrected positron emission tomography (PET) image is constructed based on the maximization of the pixel intensity of the organ of interest in the CT attenuation correction map. Incorrect attenuation correction values for PET images can be avoided by utilizing the CT attenuation correction map.

12 Claims, 5 Drawing Sheets

1

METHODS AND SYSTEMS FOR ATTENUATION CORRECTION IN MEDICAL IMAGING

BACKGROUND OF THE INVENTION

This invention relates generally to medical imaging systems, and more particularly to attenuation correction for medical imaging.

A nodule found during a computed tomography (CT) scan often requires a patient to return many months later and obtain another CT scan to determine malignancy based on a nodule doubling time. Positron emission tomography (PET) scans may be helpful in diagnosis due to increased metabolic activity in the region of the nodule. However, due to the comparatively lower resolution of PET images as compared to CT images, and due to the effects of respiratory or patient motion during a PET scan, nodule activity can be blurred in the PET scan. Consequently, it can be difficult to quantify the nodule activity with a PET scan alone, which may result in an indeterminate or incorrect outcome of the diagnosis of the nodule.

More particularly, the image quality of at least some known PET and CT systems is highly affected by physiological patient movement. Such image quality may affect diagnosis. Lung nodules, cardiac wall features or other small features of interest that move due to physiological motion such as cardiac and respiratory motion may appear blurred or even absent without proper corrections. Therefore, attenuation correction is performed, where an attenuation correction map derived from CT transmission images is used to correct the PET images. Further, misalignment of a CT attenuation map and the PET emission image that is due to respiratory motion may cause errors in attenuation correction (AC) factors and may produce artifacts in the final reconstructed AC PET image. For instance, "under attenuation correction" may have the potential of introducing artifacts that resemble artificial myocardial perfusion defects in cardiac PET. Thus, in the case of cardiac PET, wherein helical CT data is used, attenuation artifacts may result in areas having artificially reduced tracer uptake in the myocardial wall that may be incorrectly interpreted as perfusion defects by utilizing helical CT attenuation correction (CTAC) data.

BRIEF DESCRIPTION OF THE INVENTION

A method for positron emission tomography/computed tomography (PET/CT) is provided. In one embodiment, the method includes scanning an object/patient to acquire a stream of cine CT data and selecting the image having the maximum area of an organ of interest in the cine CT data as a baseline. The baseline image of the organ of interest is segmented using Hounsfield units and is compared to the remaining 4-D cine CT data images of the same organ of interest. The baseline image of the organ of interest is updated so the value of each pixel of the organ of interest represents the most dense measurement for that pixel in the organ of interest. The method includes creating a single CT attenuation correction image based on the maximized baseline image of the organ of interest.

In another embodiment, a method includes scanning an object/patient to acquire a stream of cine CT data of an organ of interest that is synchronized with a respiratory motion signal. The area of the organ of interest is maximized by utilizing Hounsfield units to create a temporal cine CT image. The method further includes acquiring non-attenuated-corrected positron emission tomography (PET) emission data of the same organ of interest. The method further provides segmenting the organ of interest in the PET data by utilizing the activity level of the radioactive tracer absorbed by the organ of interest; thereby, creating a binary mask. The binary mask is applied to the temporal CT image, and the pixels below the mask are maximized to represent the maximum density measurement for the pixels representing the organ of interest. The method further creates a single CT attenuation correction image to be projected onto PET images.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Figure 1:
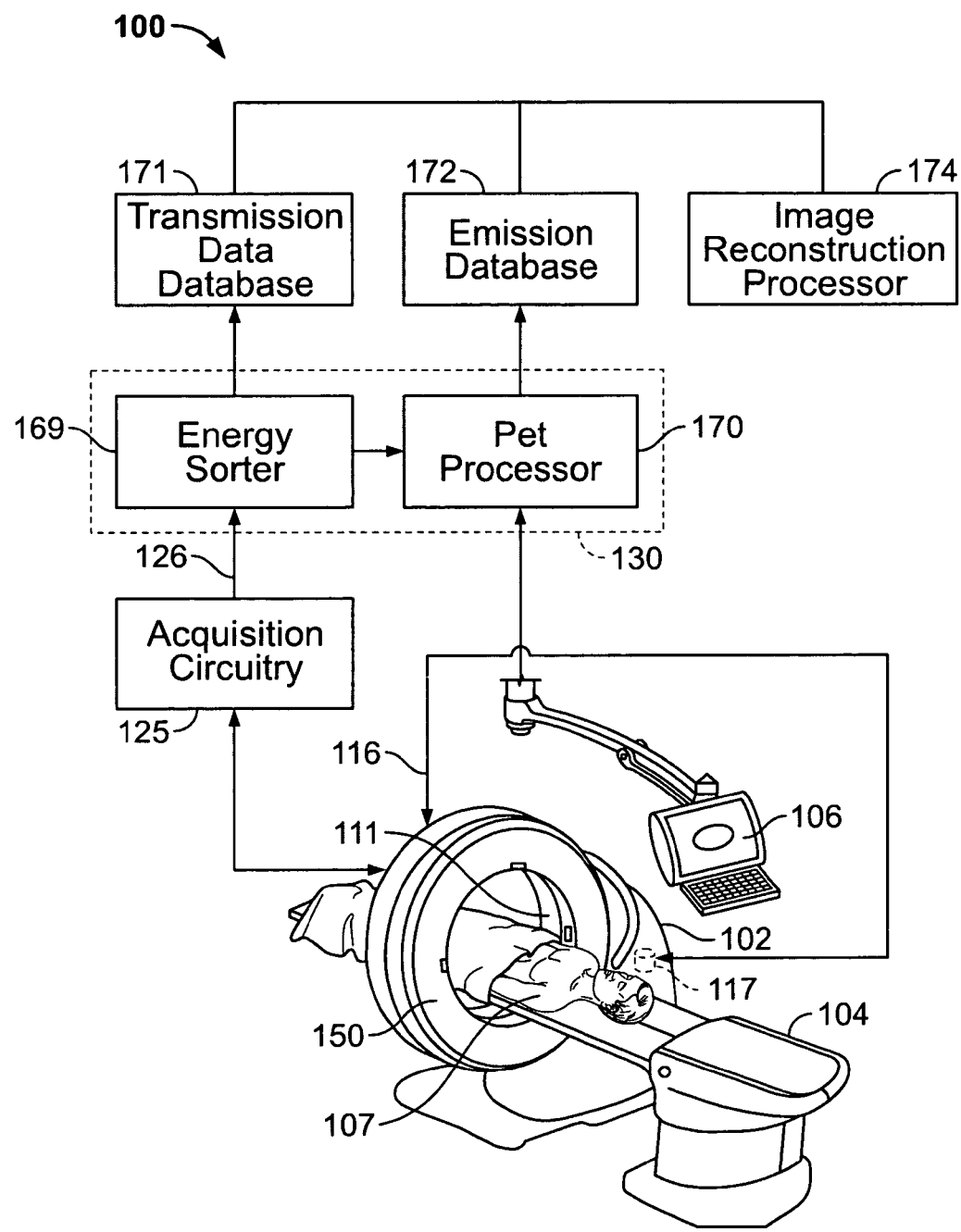
FIG. 1 is a schematic diagram illustrating a PET/CT imaging system formed in accordance with an embodiment of the present invention.

In the following detailed description, reference is made to the accompanying drawings which form a part hereof, and in which is shown by way of illustration specific embodiments in which the present invention may be practiced. These embodiments, which are also referred to herein as "examples," may be combined, or other embodiments may be utilized and structural, logical and electrical changes may be made without departing from the scope of the various embodiments of the present invention. The following detailed description is, therefore, not to be taken in a limiting sense, and the scope of the various embodiments of the present invention is defined by the appended claims and their equivalents.

In this document, the terms "a" or "an" are used, to include one or more than one. In this document, the term "or" is used to refer to a nonexclusive or, unless otherwise indicated. In addition, as used herein, the phrase "pixel" also includes embodiments of the present invention where the data is represented by a "voxel". Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, embodiments may generate (or are configured to generate) at least one viewable image.

The systems and methods are generally directed toward multi-modal medical diagnostic imaging systems capable of scanning using different modalities, such as, for example, but not limited to, Positron Emission Tomography (PET) and Computed Tomography (CT). The term "multi-modal" refers to systems that perform scans in different modalities, for example, CT and PET. It is contemplated that the benefits of systems and methods for analyzing an abnormality of an object accrue to all multi-modal imaging systems, such as, for example, but not limited to, a PET-CT imaging system, a SPECT/PET imaging system, and the like.

In the various embodiments, different imaging modalities may be used. For example, in computed tomography (CT) imaging system configurations, an X-ray source projects a fan-shaped beam which is collimated to lie within an X-Y plane of a Cartesian coordinate system and generally referred to as an "imaging plane". The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements, i.e., projection data, from the detector array at one gantry angle is referred to as a "view". A "scan" of the object comprises a set of views made at different gantry angles, or view angles, during one revolution of the X-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to define the brightness of a corresponding pixel on a cathode ray tube display.

At least some CT systems are configured to also perform Positron Emission Tomography (PET) and are referred to as PET-CT systems. PET scanners incorporate a process similar to that found in CT, in that a map of the object attenuation can be generated. A method to perform this attenuation measurement includes the use of rotation rod sources containing positron-emitting radionuclides. The rods rotate outside the patient bore, but inside the diameter of the PET detector ring. Annihilation events occurring in the rods can send one photon into a near-side detector while the pair photon traverses the object of interest in a manner similar to the CT X-ray. The data acquired from this method contains essentially the same image information as that acquired from the CT method except for the statistical quality of the resultant data. In the rotating rod case, the statistical quality is orders of magnitude inferior to most common CT scans. For the PET purpose, data acquired in this manner is used to correct for the attenuation seen in the object by the annihilation events, which is often the most substantial correction performed on the PET data.

Positrons are positively charged electrons (anti-electrons) which are emitted by radio nuclides that have been prepared using a cyclotron or another device. The radionuclides most often employed in diagnostic imaging are fluorine-18 ($^{18}F$), carbon-11 ($^{11}C$), nitrogen-13 ($^{13}N$), and oxygen-15 ($^{15}O$), among others. Radionuclides are employed as radioactive tracers called "radiopharmaceuticals" that are incorporated into substances such as glucose or carbon dioxide.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism and protein synthesis. Hereinafter, in the interest of simplifying this explanation, an organ to be imaged including a vessel will be referred to generally as an "organ of interest" and various embodiments of the invention will be described with respect to a hypothetical organ of interest.

After the radiopharmaceutical becomes concentrated within an organ of interest and while the radionuclides decay, the radionuclides emit positrons. The positrons travel a very short distance before they encounter an electron and, when the positron encounters an electron, the positron is annihilated and converted into two photons or gamma rays. This annihilation event is characterized by two features which are pertinent to medical imaging and particularly to medical imaging using PET. First, each gamma ray has an energy of approximately 511 keV upon annihilation. Second, the two gamma rays are directed in nearly opposite directions (e.g., 180 degrees apart).

In PET imaging, if the general locations of annihilations can be identified in three dimensions, a three dimensional image of radiopharmaceutical concentration in an organ of interest can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes, millions of annihilations are recorded, where each annihilation is associated with a unique detector pair. After an acquisition period, recorded annihilation data can be used by any of several different well known image reconstruction methods to reconstruct the three dimensional image of the organ of interest.

FIG. 1 is a block diagram of a medical imaging system 100 formed in accordance with an exemplary embodiment of the present invention that may perform imaging as described above. The system may be any emission-type computed tomography imaging system including, but not limited to a Positron Emission Tomography (PET) scanner, a dual PET/computed tomography (CT) scanner, a single photon emission computed tomography (SPECT) scanner or a SPECT/CT scanner, among others.

The medical imaging system 100 such as, for example, a PET system, includes a gantry 102, a patient table 104, and a computer system 106. Gantry 102 provides mechanical support for mounting devices such as, for example, detectors, scanners and transmitters that are useful for scanning a patient 107. Gantry 102 houses imaging devices such as, for example, PET detectors. The PET system may be a stationary annular detector and optionally may include a pin source for PET imaging.

The imaging devices on gantry 102 acquire image data by scanning a patient 107 lying on patient table 104. Moving patient table 104 enables the scanning of various parts of the patient 107. Patient table 104 lies along the axis of gantry 102, which is known as a viewing area axis (as shown in FIG. 1) and can be moved along this viewing area axis. Patient table 104 can be positioned at various axial positions along the viewed area axis. In an embodiment of the invention, gantry 102 includes a plurality of detectors that are fixed and spaced on gantry 102 positioned radially outward from the viewing area axis. In accordance with an embodiment of the invention, gantry 102 includes a plurality of detectors that are rotatable about the viewing area axis. This enables the scanning of various parts of the patient at different axial positions. For CT imaging, a rotating detector and an x-ray source (optionally including a stationary detector ring) may be provided.

In an embodiment of the invention, computer system 106 controls, for example, the positioning of patient table 104. Specifically, computer system 106 is programmed to position patient table 104 at a plurality of axial positions along the viewing area axis. This positioning enables the scanning of different axial positions of the patient 107. Computer system 106 may further be programmed to keep a track of the position of patient table 104. Computer system 106 is also programmed to receive image data collected during scanning. A signal-to-noise ratio (SNR) of the collected data may be determined by computer system 106. Based on the SNR, computer system 106 is programmed to control the scanning. For example, computer system 106 may control the termination of a scan based on the SNR. In accordance with various embodiments of the invention, computer system 106 includes a processor, such as a Linux® based or a Windows® based PC, for user interface and custom array processor boards for image reconstruction.

A scan time may also be fixed or predetermined, for example, by a user or computer system 106. In the case where the user fixes the scan time, computer system 106 may receive an indication of the scan time to control the scanning. In addition to providing the scan time, the user may also provide computer system 106 an indication of the location of a volume of interest. The volume of interest is that part of the patient that is to be scanned. In one embodiment, the volume of interest may be selected by a user and input to computer system 106. In various embodiments of the invention, computer system 106 controls medical imaging system 100 to acquire the transmission data and determine a volume of interest based on the transmission data. In an embodiment of the invention, computer system 106 controls medical imaging system 100 to perform, for example, at least one of a CT scan, a PET transmission scan, and a CT scout scan to acquire the transmission data. In various embodiments of the invention, computer system 106 is programmed to automatically move a volume of interest from a first position corresponding to a frame that includes a first axial periphery of the volume of interest to a second position corresponding to a frame that includes a second axial periphery of the volume of interest. In an embodiment of the invention, computer system 106 moves the volume of interest in response to a user input. In another embodiment of the invention, computer system 106 automatically moves the volume of interest based on the transmission data.

In addition, medical imaging system 100 may include a transmission source (not shown). The transmission source is located such that the signals transmitted by the transmission source pass through the volume of interest of the patient 107. The signals may get attenuated when the signals pass through a volume of interest of the patient 107. Hence, the detectors may collect data that is attenuated as data is collected after the transmission signals pass through the patient 107. The transmission source is, thus, used to acquire attenuation data relative to the patient 107. In accordance with an embodiment of the invention, computer system 106 may be programmed to generate the attenuation data relative to the patient 107 using the transmission source. Computer system 106 may further be programmed to determine the scan time for a frame of image data based on the attenuation data. Each frame of image data is a part of the image data that corresponds to an axial position of patient 107. Moving patient table 104 along the viewing area axis enables the scanning of different axial positions of patient 107. In various embodiments of the invention, computer system 106 is programmed to modulate the time at a particular location of patient table 104. This enables a user of medical imaging system 100 to increase or decrease the acquisition time of a particular region of the body.

The attenuation data is received by computer system 106. Computer system 106 may use the received attenuation data, for example, to determine the scan time for each frame of image data. Further, the scan time of short scans may be determined based on the scan time determined for each frame of image data.

Various processors, sorters, and databases are used to acquire and manipulate emission and transmission data. The processors, sorters and databases of FIG. 1 include acquisition circuitry 125, an acquisition processor 130, a transmission data database 171, an emission database 172, and an image reconstruction processor 174. In various embodiments of the invention, acquisition processor 130 is programmed to acquire emission data in the list mode and sinogram mode, as described in more detail below, and generate the image based on the emission data acquired in the list mode, the emission data acquired in the sinogram mode and the Time-of-Flight (TOF) information of the emission data. Other computing components may be included with the system, which have been omitted here in the interest of simplification.

In one embodiment, sorter 169 provides the time, location, and energy data to PET processor 170. Processor 170 generally uses the received data to identify pairs of data, also known as coincidence pairs, coincident pair lines and lines of response, corresponding to annihilation events that occurred inside the region of interest. After acquisition processor 130 identifies an annihilation event, the acquisition processor 130 updates data in emission database 172 to store information relating to the annihilation event.

After the acquisition session has been completed and complete sets of transmission and emission data have been stored in databases 171 and 172, respectively, image reconstruction processor 174 accesses the data in databases 171 and 172 and uses the accessed data to generate images that may be requested by a system operator. The operator can use computer system 106 to select image types and views.

Figure 2:
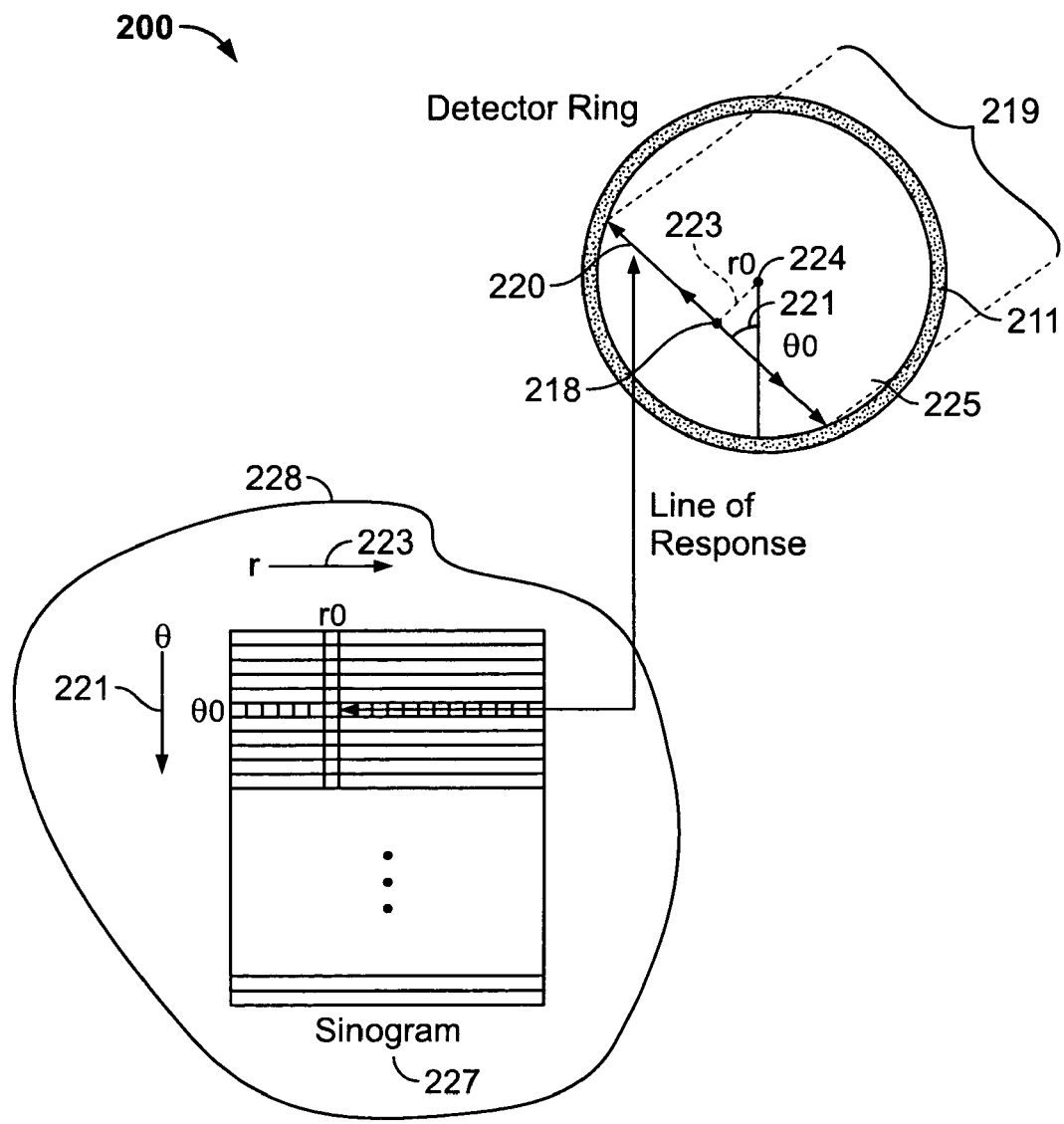
FIG. 2 is a perspective view of a detector ring and an illustration of the construction of a sinogram formed in accordance with an embodiment of the present invention.

FIG. 2 is a perspective view 200 of a detector ring 211 and an illustration 228 of the construction of a sinogram 227 formed in accordance with an embodiment of the present invention. In positron emission tomography (PET) imaging, sorter 169 (shown in FIG. 1) receives data corresponding to a coincidence event pair 219 of an annihilation event 218 and identifies a corresponding line of response 220. Each line of response 220 may be identified by an angle ($\theta$) 221 and a distance (r) 223 from a center 224 of the field of view 225. The array of the responses 220 is known as a sinogram 227.

System 100 has multiple rings 211 of detectors covering, for example, about 15-25 centimeters in the axial direction. Detectors typically include radiation detectors with sufficiently high timing resolution. The high timing resolution may be required to discriminate between at least two positions along the line of response 220 joining two such detectors. The photons are emitted in opposite direction along the line of response 220 and are simultaneously detected by detectors placed on the line of response 220.

PET data may be acquired in either a 2-dimensional or 3-dimensional mode. In 2-dimensional acquisition mode, lines of responses 220 occurring in the same ring 211 or immediately adjacent ring 211 are accepted. In the 3-dimensional mode, any line of response 220 occurring between any pair of detector rings 211 is acquired. In the 2-dimensional mode, the coincident events 219 that are acquired within the same detector ring 211 contribute to the direct planes, while those events 219 across neighboring rings 211 contribute to the cross planes.

Figure 3:
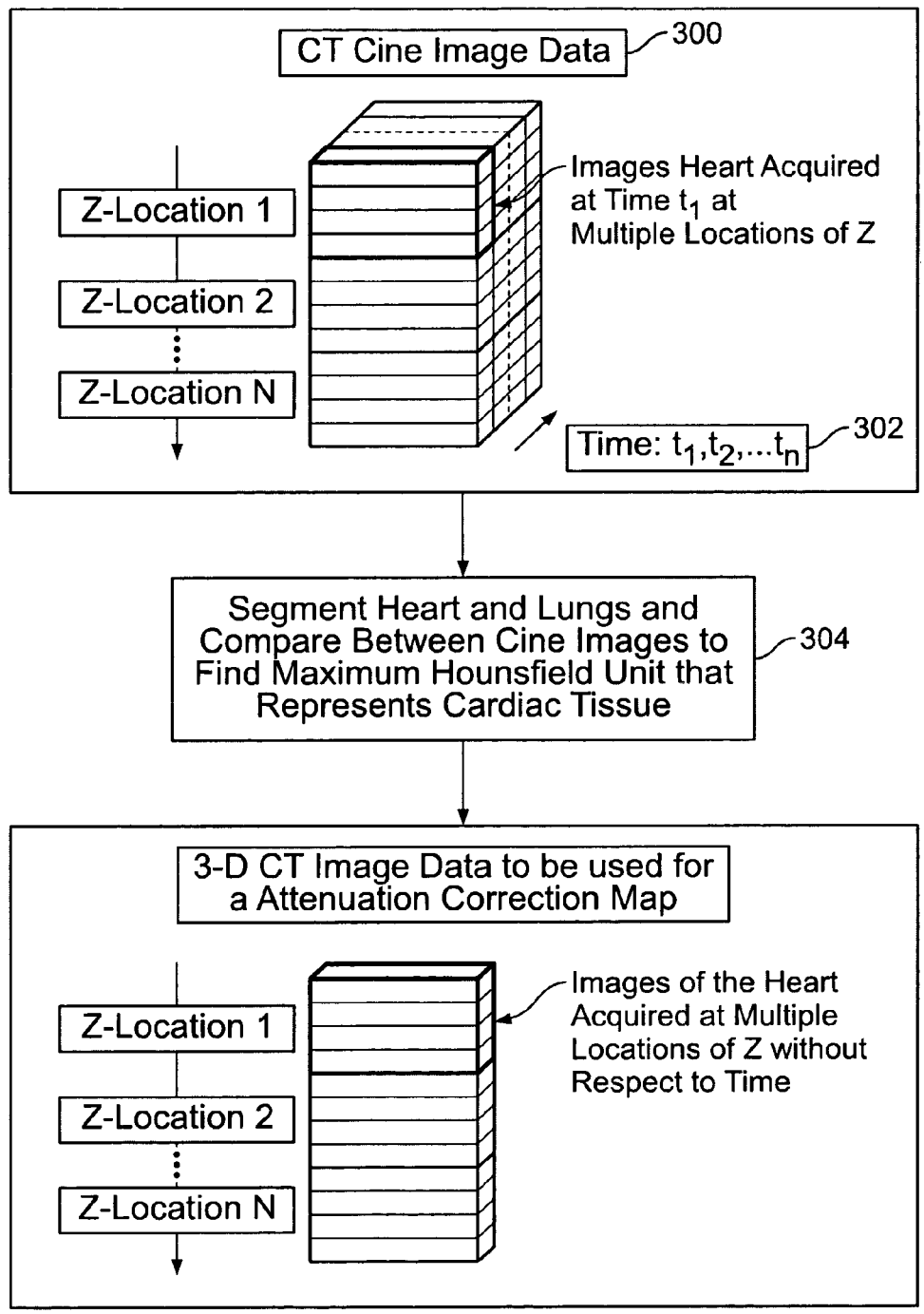
FIG. 3 is a graphic illustration depicting CT cine image data reduced from four-dimensions to three-dimensions and segmented according to an organ of interest in accordance with an embodiment of the present invention.

FIG. 3 illustrates a plurality of cine CT image frames 300 of a volume of interest (not shown) in four-dimensions (4D): x, y, and z dimensions plus time (t) 302. The 4D data is converted to three-dimensions (3D) data by removing the element of time 302. The organ of interest is segmented within the volume of interest. In one embodiment, the organ of interest is a heart. The Hounsfield unit (HU) range, which may be a predetermined or predefined range, corresponding to the organ of interest is used to segment 304 the organ of interest from surrounding tissue (e.g., segment cardiac tissue from lung tissue). The CT image frame having a maximum area for the organ of interest (e.g., having the maximum number of pixels within the defined range) is selected as a baseline image. The remaining CT images frames of the organ of interest are compared to the baseline image frame on a pixel by pixel basis, and each pixel in the baseline image frame of the organ of interest is updated to reflect the highest density HU value for that pixel. For instance, an image of the organ of interest in a second CT image frame is compared with the baseline image frame. More particularly, a particular pixel location in both images is compared. If the pixel in the second image frame has a higher HU value than the baseline pixel value, the baseline pixel value is updated. However, if the pixel in the second image frame has a smaller HU value than the baseline pixel value, the baseline pixel value is not updated. By comparing each pixel in the baseline image frame for the organ of interest with respect to all remaining image frames, the organ of interest is maximized. The 3D CT image data having a maximum intensity, which may be referred to as a composite image, for the organ of interest is used to generate an attenuation correction map using any known process.

Figure 4:
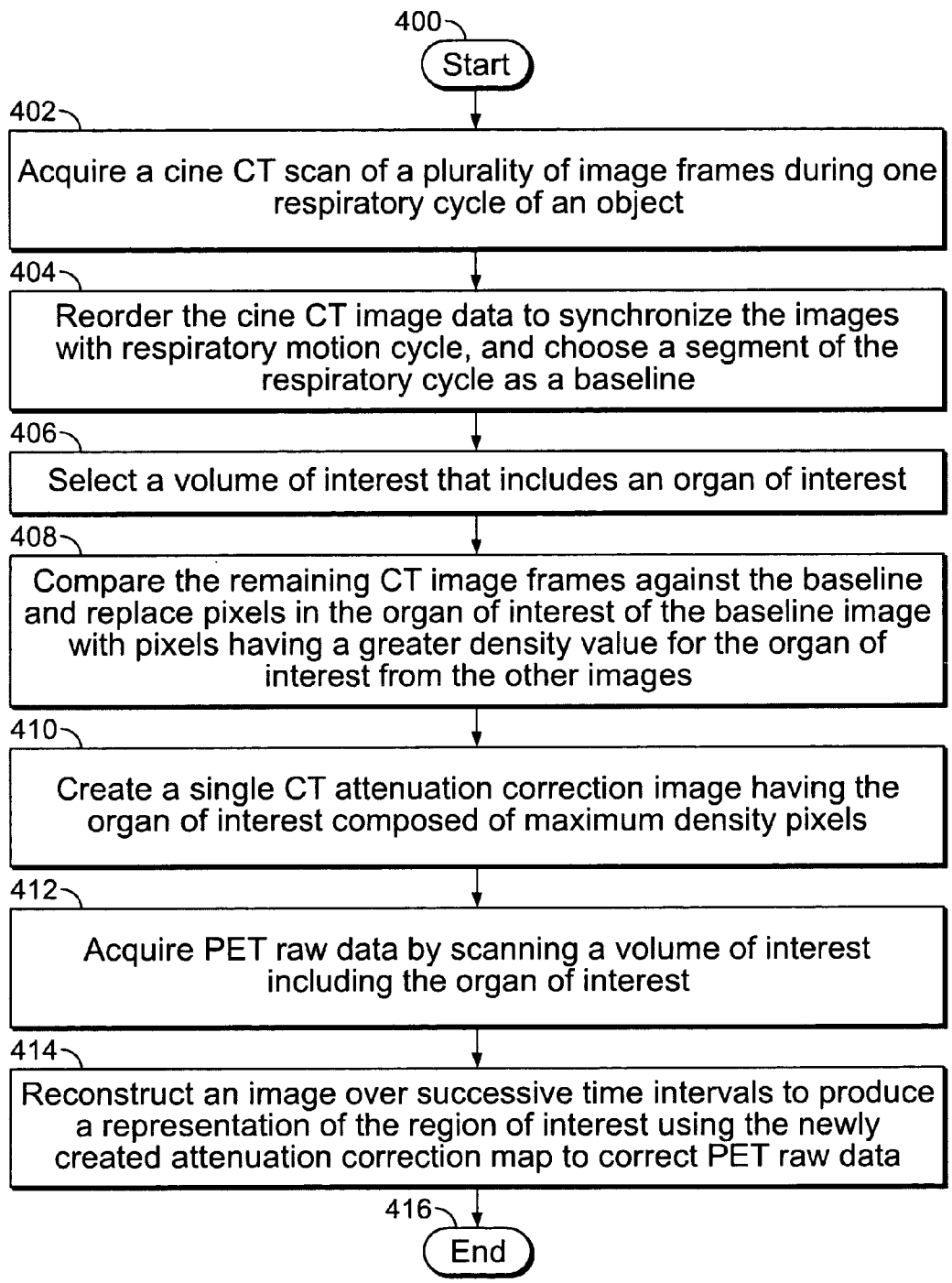
FIG. 4 is a flowchart illustrating a method for generating a cine (e.g. temporal) intensity maximum (CIM) image of an organ of interest in accordance with an embodiment of the present invention.

FIG. 4 is a flowchart for a process to create an image of a region of interest in a cardiac patient by utilizing a medical imaging system 100 in accordance with at least one embodiment of the present invention. At 400, a request to start a scan is made, for example, by computer system 100. In one embodiment, the medical imaging system 100 is a PET/CT system. An example of such a PET/CT system is a GE Discovery STE system, commercially available from General Electric Medical Systems of Waukesha, Wis. In another embodiment, the medical imaging system 100 is a SPECT scanner. The medical imaging system 100, in one embodiment, is configured to utilize low current in order to reduce an x-ray dose provided to patient 107.

At 402, the medical imaging system 100 scans patient 107 in axial steps over a successive time interval to acquire a cine CT scan having a plurality of image frames. The duration of the scan over a particular Z-location in one embodiment is one respiratory period of the patient's normal breathing rate. Alternatively, equipment to monitor the patient's respiratory motion may be also utilized where the duration of the scan over a Z-location is at least one respiratory cycle. Each axial slice location includes a time series of sequential images acquired throughout the respiratory cycle. The data is stored in memory (not shown).

At 404, the cine CT image data is reordered to synchronize the images with the patient's respiratory motion cycle. For example, conventionally respiratory gating includes utilizing a gating signal from a commercially available respiratory monitor that provides the time of maximum inspiration. In addition, the gating signal can be obtained from the motion found within the cine CT image frames. Alternatively, maximum expiration may be selected because the organs are most stable at that time. Because the cine image data is temporal, the time the image frames were acquired is known. Therefore, the image frame corresponding to a maximum inspiration or a maximum expiration may be determined, and this image frame may be chosen as a baseline image. Once the baseline image is selected, the remaining image frames will be reordered with the baseline selected as the primary image frame. Thus, for example if there are five image frames that are originally in consecutive order (e.g., 1, 2, 3, 4, and 5) and frame three is selected as the baseline, reordering will result in a new order (e.g., 3, 4, 5, 1, and 2).

At 406, a location of a volume of interest within the patient 107 that includes, for example, an organ of interest is selected by any known process. In an embodiment, the volume of interest may contain a physiological abnormality. In various embodiments of the invention, the volume of interest may be a particular region of the body of the patient 107, for example, an organ, a lesion, a nodule, a body part, and the like. The volume of interest may be identified for imaging the particular region of the body of the patient 107 for longer durations than a single respiratory cycle. In various embodiments of the invention, a volume of interest is determined by localizing the volume of interest using transmission data. In an embodiment of the invention, a CT scan may be performed to acquire the transmission data. In yet another embodiment, a CT scout scan is performed to acquire the transmission data. The CT scout scan may be performed using a scout scan feature of a CT scanner as is known in the art. An image is then generated based on the acquired transmission data. In another embodiment, the volume of interest is localized automatically using computer-aided detection algorithms, such as Computer Aided Diagnosis (CAD) algorithms as described in U.S. Pat. No. 6,574,304, entitled "Computer aided acquisition of medical images", and U.S. Pat. No. 6,687,329, entitled "Computer aided acquisition of medical images", the entire disclosures of which are hereby incorporated by reference herein. In various other embodiments of the invention, the volume of interest may be identified manually by the user of medical imaging system 100. In yet another embodiment, a location of a volume of interest within the patient 107 is determined by performing at least one CT scout scan of the patient and automatically determining the volume of interest by comparing the scan data to a predetermined feature of historical scan data.

In various embodiments of the invention, the volume of interest is moved from a first position corresponding to a frame that includes a first axial periphery of the volume of interest to a second position corresponding to a frame that includes a second axial periphery of the volume of interest. This ensures that the plurality of frames include the volume of interest when the volume of interest is axially longer than a field of view of the medical imaging system 100.

At 408, the baseline image frame is compared to the remaining CT image frames to maximize the size of the organ of interest based on Hu values. However, it should be noted that other values maybe used. The remaining CT image frames of the organ of interest are compared to the baseline image of the organ of interest, and each pixel in the baseline image of the organ of interest is updated to reflect the highest density Hu measurement for that pixel. For instance, if a pixel in the second CT image frame, for the organ of interest, has a higher density measurement (e.g., higher Hu value) compared to the baseline pixel at the same location, the baseline pixel value is updated; otherwise, the baseline pixel value is left unchanged. Thus, the organ of interest is maximized by comparing each pixel in the baseline image for the organ of interest with the remaining CT image frames for the organ of interest.

At 410, the baseline image, containing the organ of interest composed of the maximum density measurements of all the CT image frames, is used to create a single CT attenuation correction map (e.g., each pixel having the greatest Hu value is used from the various image frames). Typically medical imaging utilizes two basic modalities: transmission imaging and emission imaging. Transmission imaging includes an imaging source, for example x-rays, that are external to a patient's body and transmitted through the patient to a detector. Emission imaging, on the other hand, includes an imaging source that is internal to the patient (e.g., a radioisotope such as fluorodeoxyglucose) that is emitted from within the patient's body towards a detector.

Attenuation occurs when the radiation source passes through the patient's body and is absorbed or scattered by tissue, cartilage, or bone. For instance, radiation is absorbed by fat or breast tissue before reaching the heart. These attenuation affects can lead to false positive results. Attenuation is measured utilizing a Hounsfield scale. For example, various physiological structures have different attenuation properties. For instance, water has an attenuation of zero Hounsfield units (Hu), air is −1000 Hu, cancellous bone is typically 400 Hu, and cranial bone can be 2000 Hu, tissue such as the liver can range from −15 to +155 Hu, and cardiac tissue can range from 0 to 80 Hu. Because the amount of external radiation being transmitted to the patient during a CT scan is known and the amount of radiation detected after passing through the patient can be detected, the amount of attenuation through tissue can be calculated. However, measuring attenuation utilizing an emission source is difficult because the source of radiation is emitted from a tissue source within the subject. Because the depth, shape, and size of an organ containing the radioisotope is unknown before the PET scan, and often the emission of the particle passes through underlying or overlying tissue, that attenuation value differs. Specifically, an attenuation image of an object being scanned is obtained during the transmission period of a PET acquisition scan period or from a CT scan that precedes the PET emission acquisition. A CT attenuation correction image is utilized to correct PET images energy attenuation due to different anatomical structures.

At 412, a plurality of frames of PET emission data of patient 107 is acquired using the medical imaging system 100, such that at least one frame includes the identified volume of interest. The emission data includes information from detected annihilation photons. In various embodiments of the invention, a portion of the PET emission data may be acquired in a list mode or a sonogram mode. Further, another portion of the PET emission data may be acquired in a sinogram mode. The list mode generally refers to an acquisition mode in which each annihilation event is stored sequentially in a list mode file. The sinogram mode generally refers to an acquisition mode in which annihilation events having identical TOF are stored in sinograms. In an embodiment of the invention, a portion of the PET emission data may be acquired in the list mode for regions outside the volume of interest and a portion of emission data may be acquired in the sinogram mode for the volume of interest. In another embodiment of the invention, a portion of the PET emission data may be acquired in the list mode for regions outside the volume of interest. Further, a portion of the PET emission data may be acquired simultaneously both in list mode and sinogram mode for the volume of interest. In yet another embodiment of the invention, a portion of the PET emission data may be acquired in the list mode for every x annihilation event, where x is a positive number greater than one. For example, for regions outside the volume of interest, x may be greater than one and for regions within the volume of interest x may be equal to one to ensure that each annihilation event within the volume of interest may be acquired. In another embodiment of the invention, PET emission data may be acquired in the list mode for the entire field of view simultaneously with emission data in the sinogram mode for the volume of interest for scatter correction.

Typically, a PET scan produces images that have a lung space that is smaller compared to a typical CT attenuation correction (CTAC) map. This has resulted in misalignment of the CT attenuation map and the PET emission image for certain organs. By selecting the heart as an organ of interest, and maximizing the density measurement for the heart, the area of the lungs is reduced in the CT attenuation correction map. The resulting PET emission data and CTAC should have reduced or no tissue mismatches where the PET myocardium overlaps with the CT lung. Thus, false positive perfusion defects may be removed. At 414, computer system 106 reconstructs an image over successive time intervals of the volume of interest by utilizing the attenuation correction map to correct PET emission data. At 416, the method terminates or may be repeated at another time.

Figure 5:
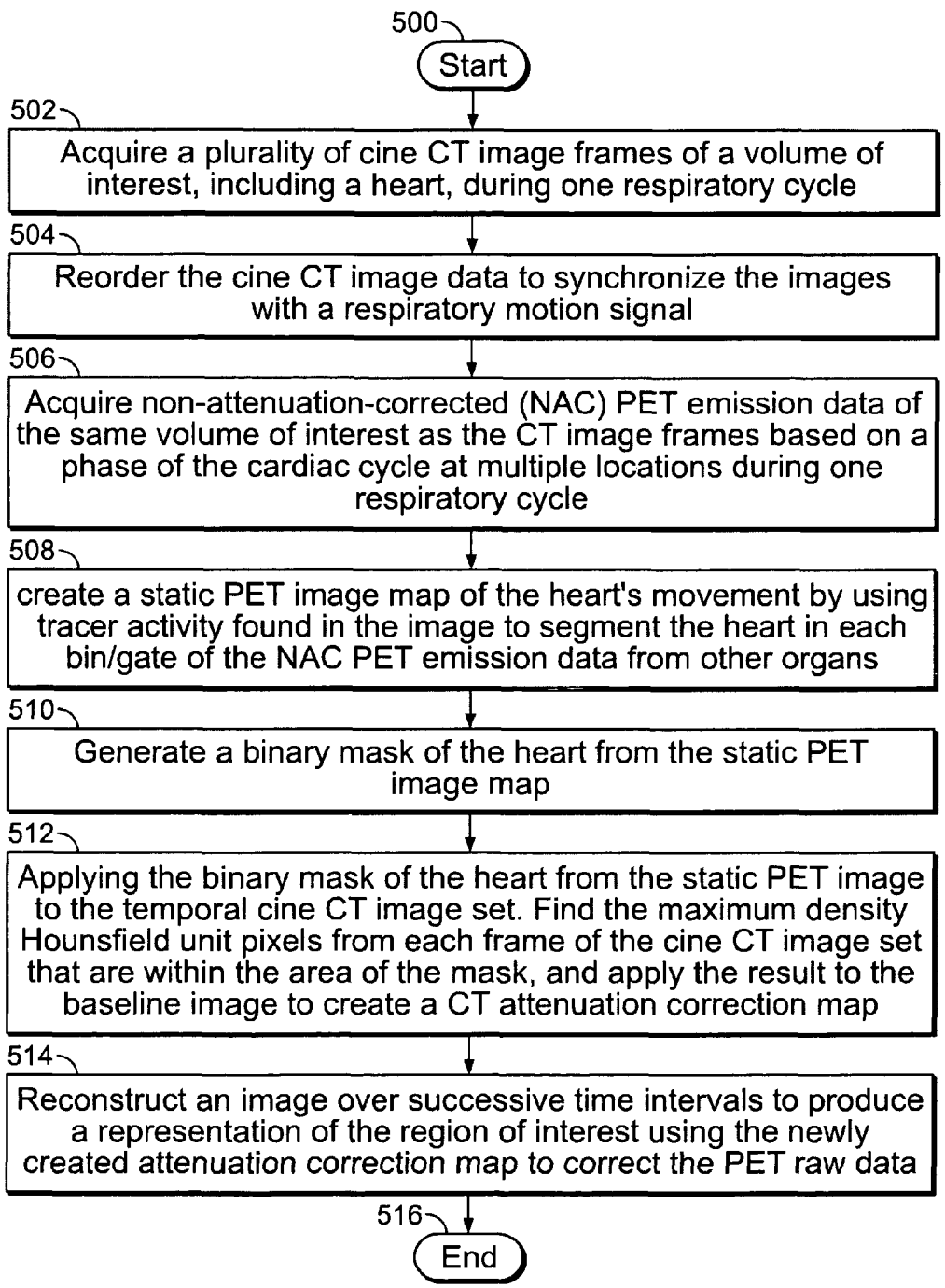
FIG. 5 is a flowchart illustrating a method to create a PET attenuation correction map that maximizes an organ of interest to align with cine CT image data in accordance with an embodiment of the present invention.

FIG. 5 is a flowchart illustrating a method to create a PET attenuation correction map that maximizes an organ of interest to align with cine CT image data. At 500, a request to start a scan is made, for example, by computer system 100. At 502, a plurality of cine CT image frames are acquired of a volume of interest during one respiratory cycle. In one embodiment, the volume of interest includes an organ of interest that is a heart.

At 504, the cine CT image data is reordered when the images are synchronized with a respiratory motion signal. The respiratory motion signal is used to order the images that all occur at the same location in Z but at different times. The images are organized for each axial slice to correspond to the time the images occur during the respiratory cycle. The axial slices match temporally with the slices that came before and after with respect to the respiratory cycle. Thus, the entire image set is synchronized in such a way that the motion due to the respiratory cycle can be modeled. The heart is segmented from the cine CT image data by utilizing the Hounsfield unit value range corresponding to cardiac tissue to produce a CT image having the largest myocardial area.

At 506, non-attenuation-corrected (NAC) PET emission data is acquired of the same volume of interest for which the cine CT image frames were acquired in 502. The PET data is acquired either as gated data (e.g., gated to a cardiac cycle such that images are acquired depending upon the heart's cycle) or via a dynamic cardiac procedure (e.g., using a PET tracer and monitoring the tracer through the body based on time). In one embodiment, gated data is acquired by acquiring PET images when the heart is at a particular location during the heart cycle, e.g., either filled with blood or completely contracted. On the other hand, PET images acquired using the dynamic cardiac procedure are acquired based on time, e.g., every ten seconds an image is taken and placed in a separate bin. Over a specified duration of time, all the bins are collected to create a three-dimensional data set.

At 508, a static PET image is created from the NAC PET emission data. If the PET emission scan was a cardiac gated scan or a dynamic scan the static PET image is created by summing the cardiac gates or the dynamic bins. An organ of interest is selected from the static PET image and by using the radioactive tracer activity found in the image, the organ of interest is segmented from the surrounding organs and tissue (e.g., segment cardiac tissue from lung tissue).

At 510, a binary mask is generated from the static PET image. The binary mask is an image with the same pixel dimensions as the original image. A region of interest (ROI) is selected using the radioactive tracer values. Pixels are labeled as either being inside the ROI (e.g., pixel value 1) or being outside the ROI (e.g., pixel value 0). A binary image is created that when multiplied by an image, the result is to display pixels that are only within that region of interest.

At 512, the binary mask is applied to the temporal cine CT image. The mask is used to determine the ROI within the cine CT image, and the maximum density of pixels in an organ of interest based on a Hounsfield unit value is found within the ROI. In one embodiment, the organ of interest is the heart, and the binary mask is used to maximize all the pixels found under the area of the heart (e.g., as an overlay on top of the CT images). Each pixel under the mask area on the cine CT image is updated to reflect the highest density Hounsfield Unit measurement for that pixel; thereby maximizing the area of the heart. By selecting the heart as an organ of interest, and maximizing the density measurement for the heart, the area of the lungs is reduced. The resulting maximized data set of the ROI is applied to the baseline image to create a CT attenuation correction map. The CT attenuation correction map includes attenuation correction factors for the myocardium at every pixel at which the myocardium appears in the PET image.

At 514, an image is reconstructed over successive time intervals to produce a representation of the ROI using the attenuation correction map to correct the PET raw data. The reconstructed image has reduced or no tissue mismatches where the PET myocardium overlaps with the CT lung. Thus, false positive perfusion defects can be removed or reduced. At 516, the method terminates or may be repeated at another time.

The various embodiments or components thereof may be implemented as part of a computer system. The computer system may include a computer, an input device, a display unit, and an interface, for example, for accessing the Internet. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

In various embodiments of the invention, the method of creating a CT attenuation correction image as described herein or any of its components may be embodied in the form of a processing machine. Typical examples of a processing machine include a general-purpose computer, a programmed microprocessor, a digital signal processor (DSP), a microcontroller, a peripheral integrated circuit element, and other devices or arrangements of devices, which are capable of implementing the steps that constitute the methods described herein.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The processing machine executes a set of instructions (e.g., corresponding to the method steps described herein) that are stored in one or more storage elements (also referred to as computer usable medium). The storage element may be in the form of a database or a physical memory element present in the processing machine. The storage elements may also hold data or other information as desired or needed. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a Hard Disc Drive (HDD) and a compact disc read-only memory (CDROM).

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

In various embodiments of the invention, the method of creating a CT attenuation correction image can be implemented in software, hardware, or a combination thereof. The methods provided by various embodiments of the present invention, for example, can be implemented in software by using standard programming languages such as, for example, C, C++, Java, and the like.

As used herein, the terms "software" and "firmware" are interchangeable, and include any computer program stored in memory for execution by a computer, including RAM memory, ROM memory, EPROM memory, EEPROM memory, and non-volative RAM (NVRAM) memory. The above memory types are exemplary only, and are thus limiting as to the types of memory usable for storage of a computer program.

The analysis described above may be performed on several different data sets. Calculations may be performed on individual slices or rings or detectors, groups of slices, all slices, or a select line of responses, specific r and θ ranges, and the like. The analyzed data set may be modified to focus on the motion of specific organs or structures. The physiological structure may include a biological organ, for example, the stomach, heart, lung or liver; a biological structure, for example, the diaphragm, chest wall, rib cage, rib, spine, sternum or pelvis; or a foreign object fiducial marker, for example, a marker placed for the purpose of gating; a tumor, or a lesion or sore, for example, a bone compression fracture.

It is to be understood that the above description is intended to be illustrative, and not restrictive. For example, the above-described embodiments (and/or aspects thereof) may be used in combination with each other. In addition, modifications may be made to adapt a particular situation or material to the teachings of the various embodiments of the invention without departing from its scope. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A method for constructing an image of an object having an organ of interest utilizing a medical imaging system, said method comprising:
   scanning an image volume of the organ of interest to acquire image data defining a plurality of image frames;
   selecting one image frame as a baseline image defining a largest area for the organ of interest;
   comparing, for the organ of interest, corresponding pixels in the other image frames with pixels in the baseline image;
   replacing pixels in the baseline image with corresponding pixels having a greater pixel density value; and
   constructing a single attenuation correction (AC) image based on a maximized combined image formed from pixels having the highest density values.

2. The method in accordance with claim 1, wherein the step of replacing each pixel comprises determining the largest Hounsfield Unit (Hu) value for the pixel location.

3. The method in accordance with claim 1, wherein the organ of interest is a heart, and said method further comprises increasing an area of the myocardium and reducing an area of the lungs.

4. The method in accordance with claim 1, wherein said method further comprises projecting said attenuation correction image onto a similar image volume of positron emission tomography (PET) data.

5. The method in accordance with claim 1, wherein said method further comprises reducing tissue mismatch by projecting said attenuation correction image onto a similar image volume of positron emission tomography (PET) data.

6. The method in accordance with claim 1, wherein said method further comprises reducing a number of artifacts by projecting said attenuation correction image onto a similar image volume of positron emission tomography (PET) data.

7. The method in accordance with claim 1, wherein said scanning comprises performing at least one of a positron emission tomography (PET) scan of the object, a computed tomography (CT) scan of the object, and a single photon emission computed tomography (SPECT) scan of the object.

8. The method in accordance with claim 1, wherein said method further comprises reconstructing an image of the volume of interest based on said maximized baseline image.

9. The method in accordance with claim 1, wherein said scanning the object is performed in axial steps over successive time intervals.

10. The method in accordance with claim 1, wherein said scanning the object is performed during at least one complete respiratory cycle.

11. The method in accordance with claim 1, wherein said method further comprises selecting a volume of interest having a physical abnormality in a cine CT data set formed from the plurality of image frames.

12. The method in accordance with claim 1, wherein said volume of interest comprises a anatomical structure that includes at least one of a biological organ, a biological structure, a foreign object fiducial marker, a tumor, and a lesion.

* * * * *